(12) United States Patent
Carriere Lluch

(10) Patent No.: US 9,827,072 B2
(45) Date of Patent: Nov. 28, 2017

(54) METHOD OF ASSEMBLING A DISTALIZER

(71) Applicant: ORTHODONTIC RESEARCH AND DEVELOPMENT, S.L., Barcelona (ES)

(72) Inventor: Luis Carriere Lluch, Barcelona (ES)

(73) Assignee: ORTHODONTIC RESEARCH AND DEVELOPMENT, S.L., Barcelona (ES)

(*) Notice: Subject to any disclaimer, the term of this patent is extended or adjusted under 35 U.S.C. 154(b) by 291 days.

(21) Appl. No.: 14/388,768

(22) PCT Filed: Mar. 28, 2013

(86) PCT No.: PCT/EP2013/056685
§ 371 (c)(1),
(2) Date: Sep. 26, 2014

(87) PCT Pub. No.: WO2013/144283
PCT Pub. Date: Oct. 3, 2010

(65) Prior Publication Data
US 2015/0118633 A1    Apr. 30, 2015

(30) Foreign Application Priority Data
Mar. 30, 2012   (EP) .................................... 12382119

(51) Int. Cl.
*A61C 3/00* (2006.01)
*A61C 7/02* (2006.01)
(Continued)

(52) U.S. Cl.
CPC .................. *A61C 7/02* (2013.01); *A61C 7/12* (2013.01); *A61C 7/36* (2013.01); *Y10T 29/49568* (2015.01)

(58) Field of Classification Search
CPC .... A61C 7/02; A61C 7/12; A61C 7/36; Y10T 29/49568
See application file for complete search history.

(56) References Cited

U.S. PATENT DOCUMENTS 4,235,558 A * 11/1980 Snyder .................... B62D 7/18
403/130
4,256,097 A * 3/1981 Willis ................... A61F 5/0123
602/16

(Continued)

FOREIGN PATENT DOCUMENTS

EP          1 433 435        6/2004
EP          1 649 824        4/2006

OTHER PUBLICATIONS

International Search Report and Written Opinion for PCT/EP2013/056685, dated Jun. 28, 2013, 9 pgs.

*Primary Examiner* — Heidi M Eide
(74) *Attorney, Agent, or Firm* — Squire Patton Boggs (US) LLP

(57) ABSTRACT

Method of assembling a distalizer comprising a mesial element and a distal element, and an arm connecting the distal element with the mesial element, the arm comprising a ball member at one end of the arm and the distal element comprising a receptacle for receiving said ball member, the method comprising providing the distal element with an opening of the receptacle that is large enough to introduce the ball member substantially without deformation, providing the arm with the ball member, introducing the ball member into the receptacle, and reducing the opening of the receptacle. The disclosure further relates to a distalizer obtainable by such a method.

12 Claims, 6 Drawing Sheets

(51) Int. Cl.
*A61C 7/36* (2006.01)
*A61C 7/12* (2006.01)

(56) References Cited

U.S. PATENT DOCUMENTS

| | | | |
|---|---|---|---|
| 5,120,218 A | 6/1992 | Hanson | |
| 5,620,321 A | 4/1997 | Thornburg et al. | |
| 5,738,514 A * | 4/1998 | DeVincenzo | A61C 7/36 433/18 |
| 2004/0197725 A1 * | 10/2004 | Lluch | A61C 7/14 433/18 |
| 2005/0132769 A1 * | 6/2005 | Parker | B21K 1/762 72/358 |
| 2007/0218415 A1 * | 9/2007 | Lluch | A61C 7/00 433/7 |
| 2009/0118772 A1 * | 5/2009 | Diederich | A61B 17/8685 606/301 |
| 2010/0092905 A1 * | 4/2010 | Martin | A61C 7/00 433/18 |

* cited by examiner

METHOD OF ASSEMBLING A DISTALIZER

The present invention relates to a method of assembling a distalizer, and more particularly relates to a method of assembling a distalizer that comprises at least two elements: a mesial element destined to be fixed to the surface of an upper canine, and a distal element destined to be attached to the surface of an upper molar, in particular the upper first molar.

BACKGROUND ART

Depending on a patient's malocclusion, a variety of orthodontic treatments is available. In some of these treatments, extraction of teeth may be required in order to create space for the remaining teeth. In some treatments, a distalizing element may be used, possibly in combination with the extraction of one or more teeth.

A particular distalizing element is known from e.g. EP 1 433 435 and EP 1 649 824. These distalizers are especially adapted for the segmental distalization of the canine-to-molar posterior maxillary area. The distalizers of these documents comprise a mesial element which may be fixed by its base to an upper canine, and further comprises a distal element which may be fixed by its base to an upper molar, in particular the first molar.

The mesial element in these designs comprises both a base, and an arm that connects it to the distal element. The arm may be substantially arch shaped and may comprise a ball member at one of its ends. This ball member is received in a receptacle of the distal element that has a complementary shape to the ball member.

The mesial element may comprise a blunt projection that extends substantially forwards which may serve as a hooking element. In use, a bracket with a hook may be attached to a mandibular molar and an (orthodontic) rubber band may be suspended around this hook and the hooking element on the mesial element.

This way, a force pulling the maxillary canine backwards is provided. If the patient is wearing e.g. a splint (or another fixation device) that acts as a solid anchor and fixes the teeth of the mandible in position, it may be ensured that the teeth in the mandible do not move forwards, and that the maxillary canine is pulled backwards.

Due to the connection between the mesial element and the distal element of the distalizer, the maxillary molar may thus also be pushed backwards. At the same time, due to the shape of the arm in between the canine and the molar and due to the position of the distal element on the molar, a rotational force is also exerted upon the molar. This rotational force may result in a pivot about the palatal root of the maxillary molar. Also, a rotation in the distal direction of the molar ("uprighting") may result. Thus a backwards force and a rotational force may be exerted upon the molar at the same time.

In order to avoid that the maxillary molar rotates too much in the distal direction (i.e. in this case, it would assume an orientation in which it is tilted backwards), the shape of the receptacle and the ball member are such that with a predetermined rotation of the ball member with respect to the upper molar, the ball member touches the inside of the receptacle and cannot rotate further. To this end, both the mesial element and distal element are mounted at the right height on the molar and canine and are mounted substantially straight along the locally defined mandible-maxilla (straight up-down) direction on the surface of the tooth. The arm is provided at a predefined angle with respect to the ball element. When both the canine and molar are actually straight, this angle will make sure that the ball member touches the border of the receptacle and cannot rotate further.

Similarly, the shape of the ball member and the border of the receptacle may be such that a rotation of the upper molar around its palatal root may be limited. Once a predetermined rotation is reached, the ball member may touch the border of the receptacle and not be able to rotate further.

It may thus be ensured that a distalization of the canine-molar segment may be combined with a proper (re)orientation of the set of teeth in the maxillary posterior region.

It is thus important that the ball member fits well in the receptacle of the distal segment.

It is furthermore important that the ball member once inserted in the receptacle stays in the receptacle and cannot slip out.

In the prior art, the method of assembling the distalizer comprises providing both the distal element and the mesial element of the distalizer, the arm connecting both elements being integrally formed with the mesial element. A receptacle is foreseen in the distal element and the receptacle comprises an opening for the introduction of the ball member at the end of the arm.

The ball element is slightly larger than the opening of the receptacle. The ball element is pushed into the receptacle. Upon introduction, the ball element and the border of the receptacle experience some deformation so that the ball is able to enter into the receptacle. This deformation may be mostly elastic, but the ball element could be slightly damaged. Given the importance of the ball element in the functioning of the distalizer, it is very important that the dimensions of the ball element and receptacle are well defined. The forced introduction of the ball element in the receptacle may thus cause a problem.

Additionally, it is possible for the ball element to slip out of the receptacle.

U.S. Pat. No. 5,620,321 discloses a telescoping mandibular device. The appliance comprises a pair of telescoping devices that attach on one end to the maxillary arch via a modified ball and socket device and on the other end to the mandibular arch via a modified ball and socket device. During assembly of the appliance in the mouth of the patient, after introduction of a ball in the mandibular socket, pliers may be used to plastically deform the mandibular socket legs.

U.S. Pat. No. 5,120,218 discloses an orthodontic traction device comprising a connection member and two attachment members. An attachment member may be produced with a slot that is transversely enlarged to be of approximately oval shape with its width at the minor axis just enough to permit the head of the pin to pass through it. Thereafter, with the pin in place the orthodontist applies the beak surface of a pair of jaws to the opposite sides of the device and squeezes to crimp the member and move the two sides toward one another until the jaw stop surfaces meet, when the sides of the slot will be parallel and able to retain the headed pin therein.

Both these prior art documents disclose the use of pliers (or similar) to apply force on both sides of an orthodontic device and deform it. Such a method of deformation is unsuitable for the distalizing element as herein described. The proper functioning of the distalizer is based on the collaboration between the surfaces of the ball member and the receptacle, which define collision points and upon which the distalizing effect is dependent. A proper treatment of a malocclusion with a distalizer would not be possible if either the ball member of the receptacle had an imperfection.

There thus exists a need to improve the method of manufacture and/or assembly of the distalizer that avoids or reduces these potential problems.

SUMMARY

According to a first aspect, a method of assembling a distalizer is provided. The distalizer comprises a mesial element and a distal element, and an arm connecting the distal element with the mesial element, the arm having a ball member at one end of the arm and the distal element having a receptacle for receiving said ball member. The method comprises providing the distal element with an opening of the receptacle that is large enough to introduce the ball member without substantially having to deform either the ball member or the border of the receptacle. The method further comprises providing the arm with the ball member, and introducing the ball member into the receptacle. After introduction of the ball member into the receptacle, the opening of the receptacle is reduced.

In this aspect, it can be accomplished that the ball member can be relatively easily inserted in the receptacle, and that it does not suffer deformation during this insertion. By reducing the opening of the receptacle after its introduction, damage to the ball member may be prevented and additionally it may be ensured that the ball member cannot exit the receptacle after insertion.

In certain implementations, reducing the opening of the receptacle may comprise plastically deforming the border of the receptacle to reduce the opening of the receptacle. The distal element may thus be manufactured in a single step, e.g. by molding or micro injection molding. After introduction of the ball member, the opening of the receptacle may be reduced in a relatively simple deformation step and the distalizer may be ready for use.

In some embodiments, the opening of the receptacle is at least partially delimited by a flange, and plastically deforming the receptacle comprises pushing the flange inwards. Optionally, the flange may be located substantially at a top portion of the opening of the receptacle.

In some embodiments, plastically deforming the receptacle comprises plastically deforming only a portion of the boarder of the receptacle. Local "pointwise" deformation may be enough to make sure the ball member cannot exit the receptacle.

An example of plastically deforming the border of the receptacle comprises coining.

In some embodiments, plastically deforming the border of the receptacle may comprise heating up the border. In other embodiments, the deformation of the border may take place at room temperature. Depending on the deformation, and depending on the materials used, heating of the components may be appropriate.

In some embodiments, the distalizer may be made from metal. In other embodiments, the distalizer may be made from polymer. Furthermore, the distalizer may be "hybrid", i.e. the mesial element may be made from polymers and the distal element may be made from metal.

Optionally, reducing the opening of the receptacle may comprise adding an additional border element to the border of the receptacle. By adding an additional border element, the opening of the receptacle may be reduced. No deformation of any element would be needed in this case. Such an additional border element may be added by e.g. chemically bonding or welding or even gluing. The additional border element may be of the same material as the distal element. Alternatively, the additional border element may be of a different material, for example a ceramic material, as long as a secure bond can be established.

In a further aspect, the present disclosure provides a distalizer obtainable by methods substantially as hereinbefore described.

Additional objects, advantages and features of embodiments of the invention will become apparent to those skilled in the art upon examination of the description, or may be learned by practice of the invention.

BRIEF DESCRIPTION OF THE DRAWINGS

Particular embodiments of the present invention will be described in the following by way of non-limiting examples, with reference to the appended drawings, in which.

DETAILED DESCRIPTION OF EMBODIMENTS

Figure 1:
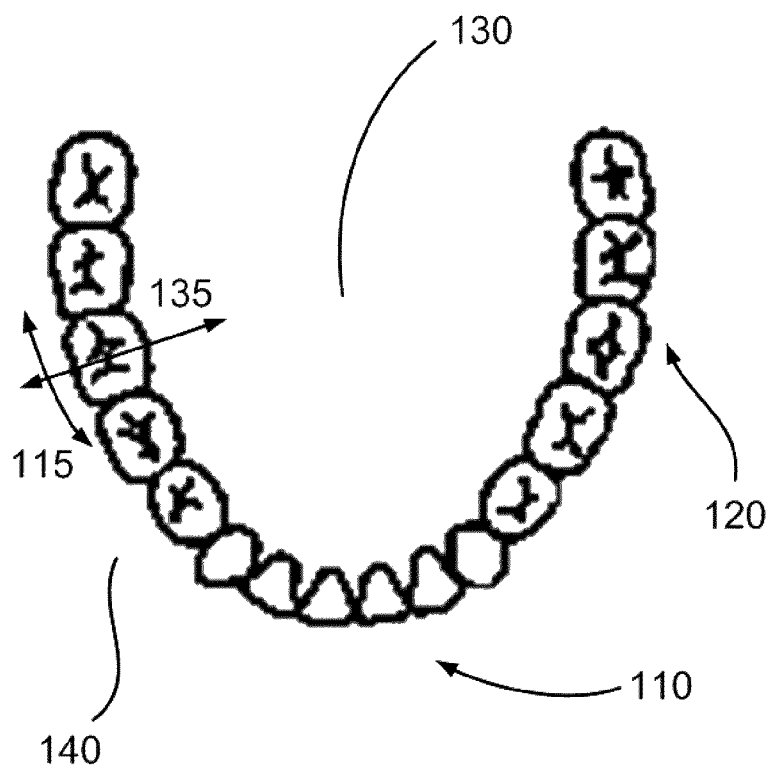
FIG. 1 illustrates some of the terminology used herein.

FIG. 1 schematically illustrates the arrangement of teeth in the lower jaw (mandible). A front portion of the mouth 110 may be referred to as a mesial region. A rear portion of the mouth 120 may be referred to as a distal region. An inner portion of the mouth behind the teeth 130 may be referred to as a lingual region. An outer portion of the mouth 140 may be referred to as a labial region. A mesial-distal direction 115 with respect to a specific tooth (first molar) has been schematically indicated in FIG. 1. Also indicated in FIG. 1 is a lingual-labial direction 135 with respect to the same tooth. This terminology will be adhered to in the present disclosure.

Figure 2A:
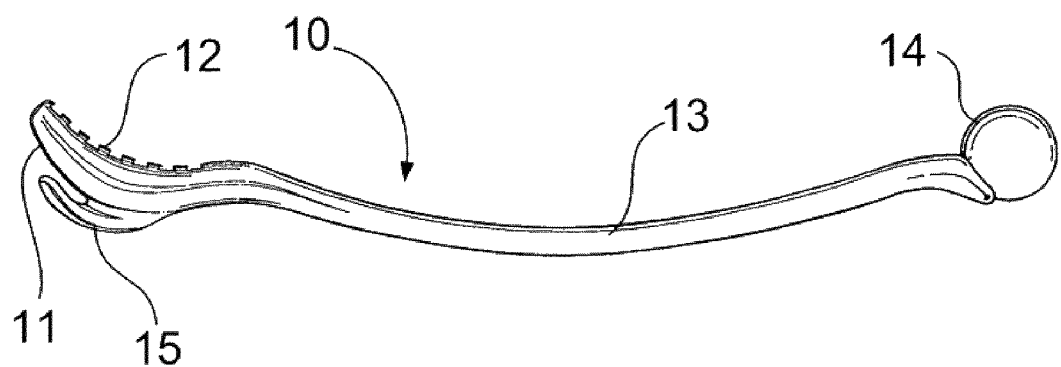
FIGS. 2a-2c illustrate a distalizer according to some embodiments.
Figure 2B:
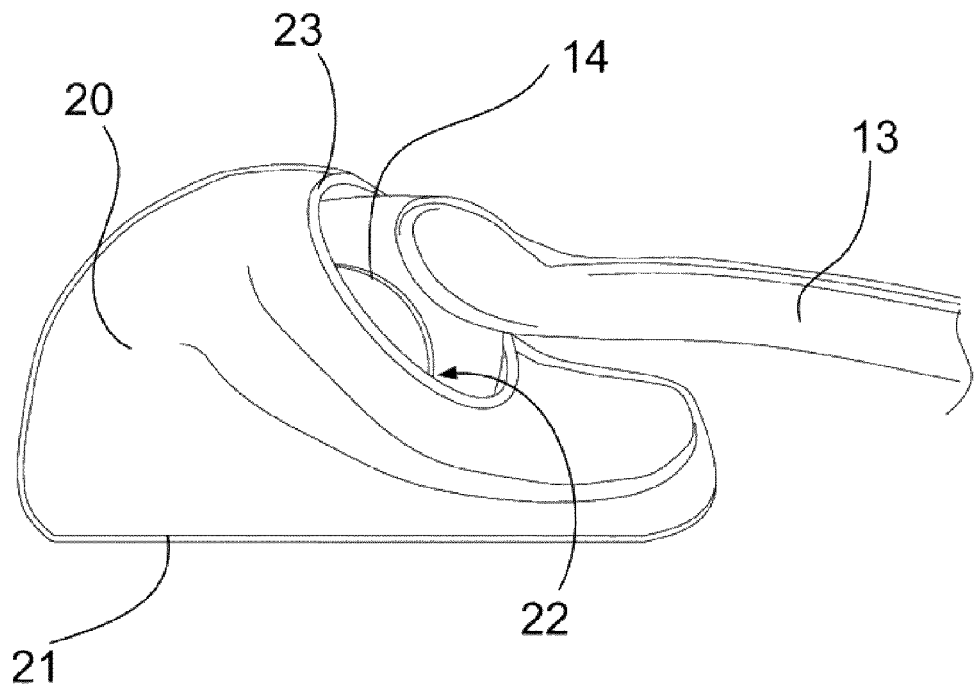
Figure 2C:
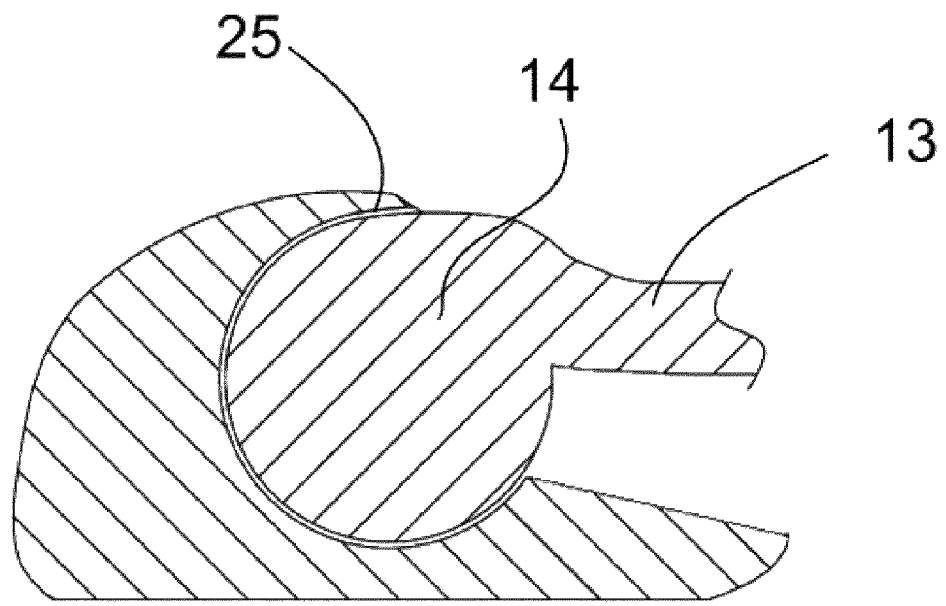

FIG. 2a-2c illustrate a distalizer adapted for the segmental distalization of the canine-to-molar posterior maxillary area. FIG. 2a illustrates a mesial element 10 comprising a mesial base 11 with an arm 13 integrally formed with the mesial element. The mesial element comprises a base surface 12 which is adapted to be fitted on a maxillary canine. The base may comprise a surface that is particularly suited for retention on the tooth once attached using adhesives. In the illustrated embodiment, a number of dovetail protrusions are incorporated for this purpose. However, other retention elements may be provided.

The hook 15 may be formed as a blunt forward (in the mesial direction) extension on the outer surface of the base 11. An elastic element, such as e.g. a rubber band may be fitted around hook 15 for providing a "backwards" (mesial-distal direction) pulling force.

At the distal end of the arm 13, a ball element 14 is arranged. The ball element is introduced in a receptacle 22 formed in the distal element 20. The distal element 20 comprises a base surface 21 adapted to be fitted on a maxillary molar, preferably the first molar. A border edge 23 of the receptacle provides collision points to limit rotation of the molar around its palatal root. The inside of the receptacle defines further collision points to limit the backwards rotation of the molar.

FIG. 2c illustrates a cross-section of the receptacle and the ball member 14. Reference sign 25 indicates an opening of the receptacle.

The distalizer may be made from any suitable material, such as e.g. metal (alloys) or polymers: the polymers may be fiber-reinforced or not. The different elements of the distalizer may also be made from different materials. For example, the mesial element may be made from a polymer, and the distal element may be made from a metal (alloy).

The distal element and the mesial element may be manufactured in various ways. The elements may be molded, both when they are made from metals or polymers. When they are made from metals, they may also be made by machining, e.g. by milling or cutting. The ball element may be integrally formed with the arm or alternatively could be welded to the arm.

Figure 3A:
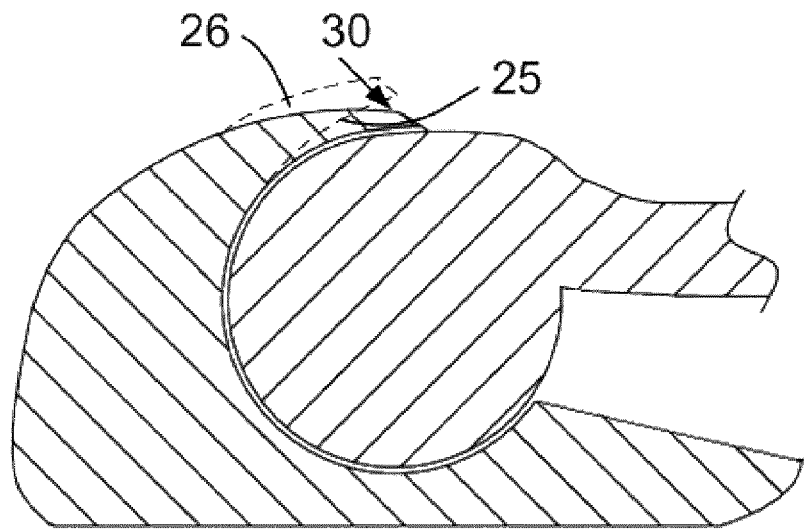
FIGS. 3a-3d illustrate various embodiments of the present invention.

FIG. 3a illustrates a first method of assembling in accordance with embodiments of the invention. The distal element comprises a receptacle with an opening 25 that is large enough for introduction of the ball member. Preferably, there is no plastic deformation of either the border of the receptacle or the ball member during introduction. As such, any damage to these elements may be minimized.

A flange 26, shown in interrupted line, which partially delimits the opening of the receptacle extends slightly outwards (i.e. in the labial direction). Once the ball member has been introduced in the receptacle, the flange 26 may be plastically deformed, i.e. the flange may be pushed inwards in direction 30. As a result, the opening of the receptacle is smaller than before the introduction of the ball member, and it is impossible for the ball member to slip out of the receptacle.

The plastic deformation may be carried out at room temperature, especially when the distalizer is made from metal. The deformation of the border of the receptacle may involve e.g. stamping, punching or coining.

The plastic deformation may also be carried out after heating up of the distalizer. This may be especially suitable when the distalizer elements are made from polymers.

In the embodiment shown in FIG. 3a, the flange extends substantially outwards from the distal element before the deformation. After plastic deformation, it is substantially flush with the rest of the border of the receptacle. In alternative embodiments, the flange may be substantially flush with the remainder of the border before deformation, and extends substantially inwards after deformation.

Figure 3B:
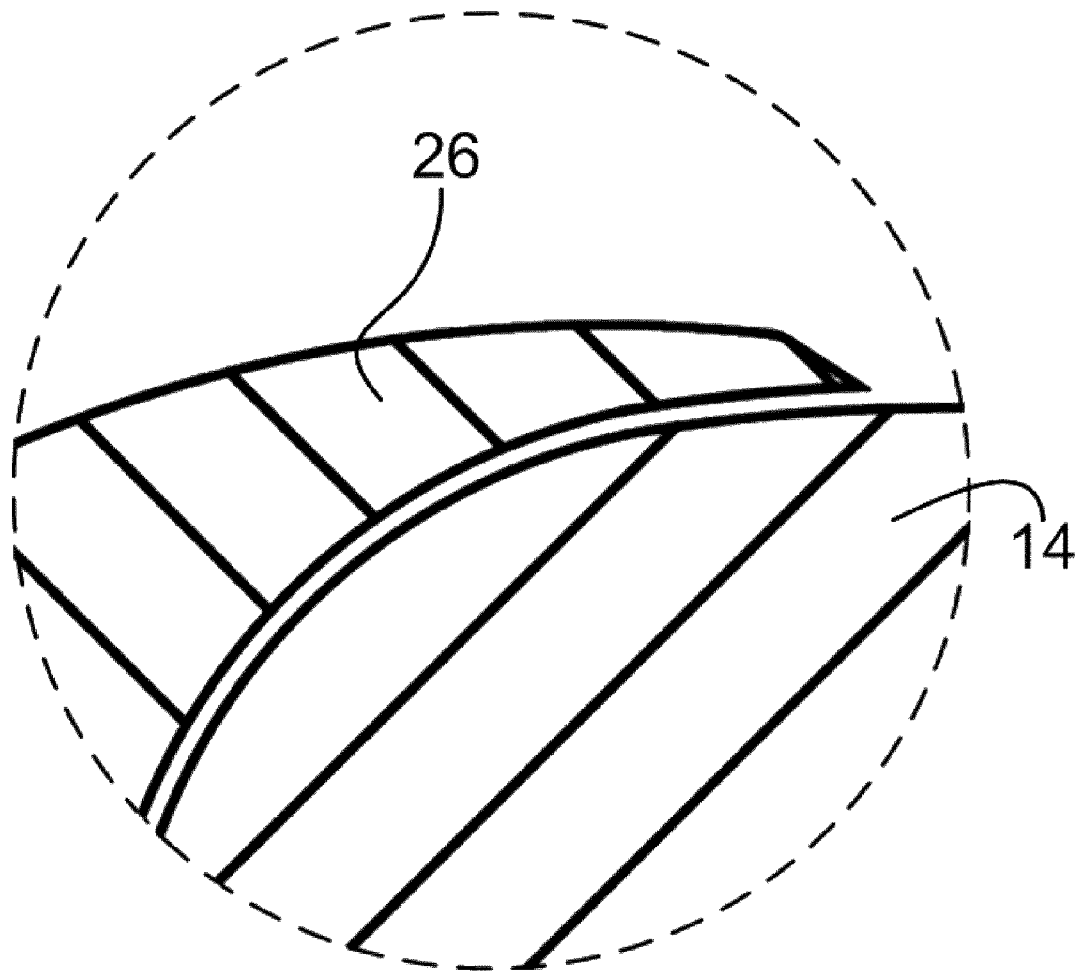

FIG. 3b illustrates in detail the resulting portion of the border of the receptacle.

Figure 3C:
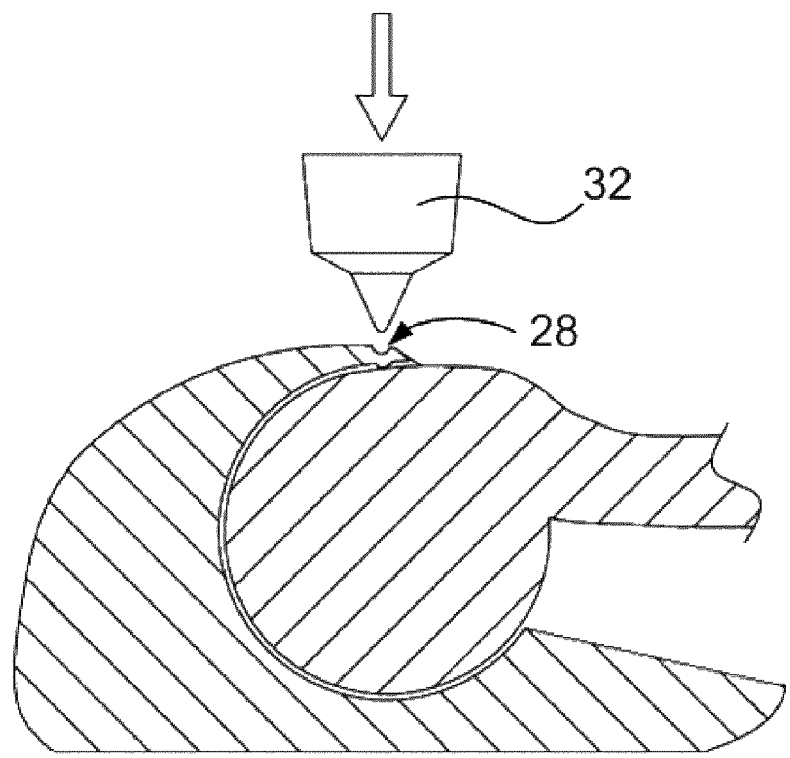

Alternative embodiments are illustrated in FIG. 3c. Instead of deforming a flange, or a substantial portion of the border of the receptacle, only a portion of the flange is deformed, or only a portion of the border is plastically deformed after introduction of the ball member. A mechanical deformation using very precise stamping may provoke a local depression that is sufficient to keep the ball member in the receptacle.

Figure 3D:
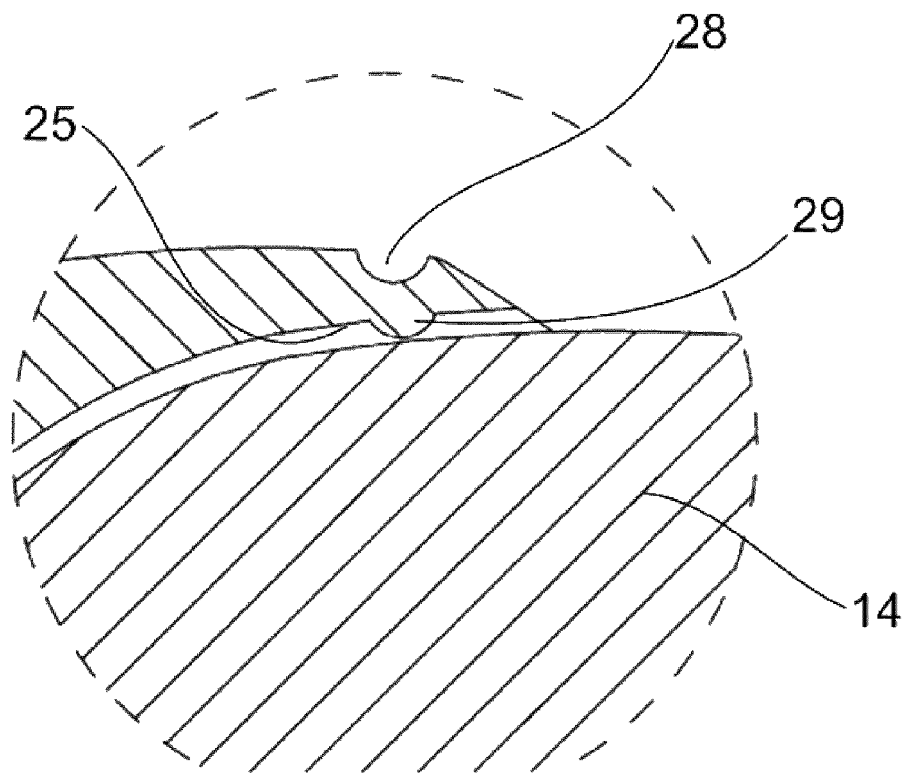

FIG. 3d illustrates in detail the local deformation of the edge of the opening 25. The depression 28 on the outer surface results in an inward protrusion 29 that delimits the receptacle and makes it impossible for the ball member to come out of the receptacle.

Figure 4A:
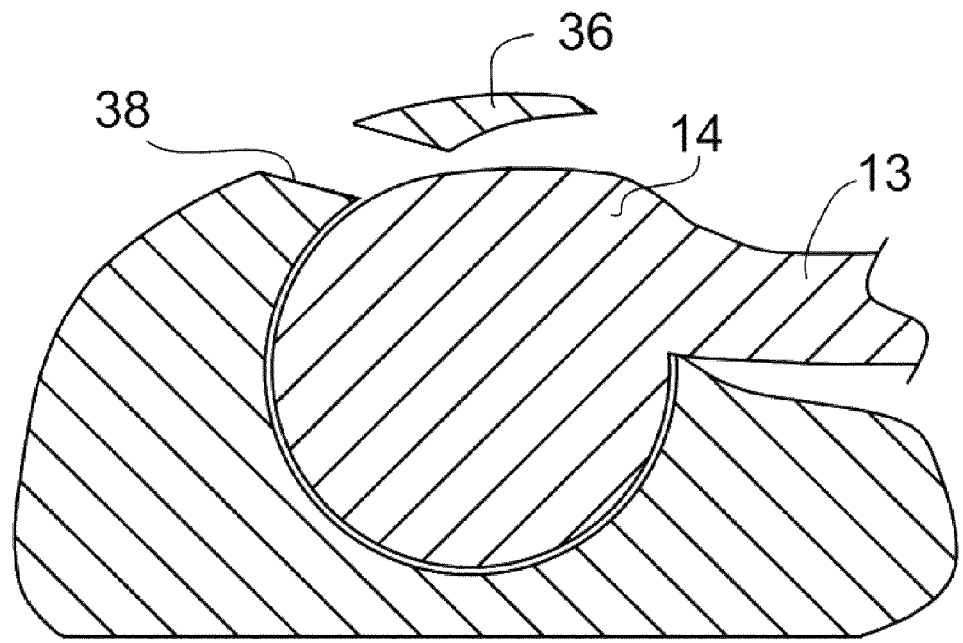
FIGS. 4a and 4b schematically illustrate further embodiments of the present invention.
Figure 4B:
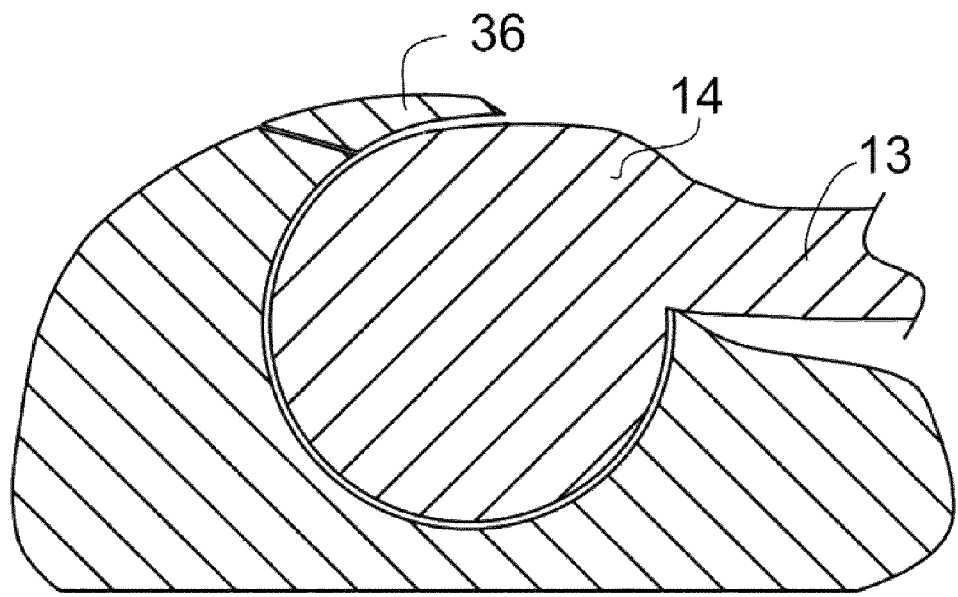
Figure 5:
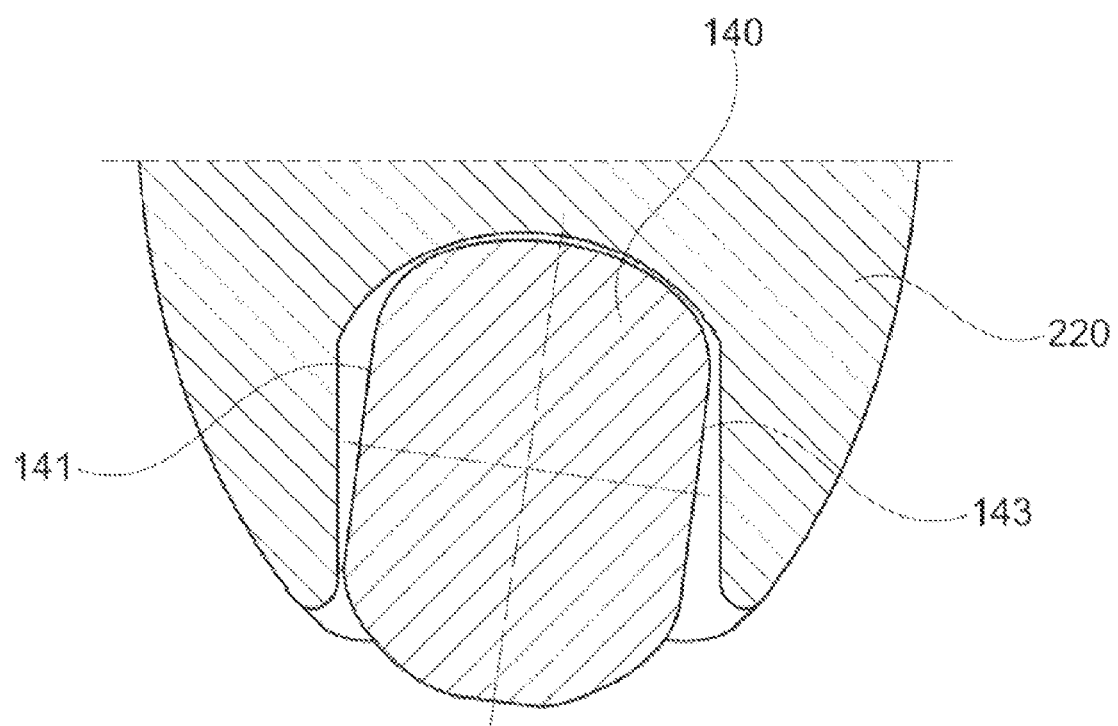
FIG. 5 illustrates a cross-section of a ball member 140 and receptacle 220. The ball member 140 is substantially spherical with two diametrically opposed planar surfaces 141, 143 and the receptacle 220 has a shape that is substantially complementary to the shape of the ball member.

FIGS. 4a and 4b schematically illustrate further embodiments. FIG. 4a illustrates the ball member 14 at the end of arm 13 after being introduced into the receptacle of the distal element. The opening of the receptacle is large enough for this introduction, without either the ball member of the border of the receptacle being deformed substantially.

After this introduction, the additional border element 36 may be attached to edge 38 of the border of the receptacle. By adding border element 36, the resulting opening of the receptacle is reduced. The ball member will thus be enclosed within the receptacle. FIG. 4b schematically illustrates the result after adding the border element. The border element may be made from any suitable material as long as a strong attachment is established with the distal element.

The additional border element may e.g. be welded, or chemically bonded to the distal element. Alternatively, a mechanical connection between the border of the receptacle and the additional border element, e.g. involving an interlocking of a male and female portion, may also be used. Such a mechanical connection may also be combined with e.g. bonding or adhesives.

Although only a number of particular embodiments and examples of the invention have been disclosed herein, it will be understood by those skilled in the art that other alternative embodiments and/or uses of the invention and obvious modifications and equivalents thereof are possible. Furthermore, the present invention covers all possible combinations of the particular embodiments described. Thus, the scope of the present invention should not be limited by particular embodiments, but should be determined only by a fair reading of the claims that follow.

The invention claimed is:

1. A method of assembling a distalizer prior to placing the distalizer in a mouth of a patient, the method comprising:
   providing an arm connecting a distal element with a mesial element, the mesial element having a base for attachment to an upper canine and the distal element having a base for attachment to an upper molar,
   providing the arm with a ball member at one end thereof,
   providing a receptacle with a receptacle opening that is at least partially delimited by a flange, the receptacle opening being large enough to introduce the ball member into the receptacle without substantial deformation of the receptacle, and the receptacle has a shape that is complementary to the shape of the ball member,
   introducing the ball member into the receptacle, and
   deforming only a portion of the flange inwards to reduce the opening of the receptacle.

2. The method according to claim 1, wherein the flange is located substantially at a top portion of the opening of the receptacle.

3. The method according to claim 1, wherein the deforming the flange comprises at least one of the following: stamping, punching and coining.

4. The method according to claim 1, wherein the deforming the flange comprises heating a border of the receptacle.

5. The method according to claim 1, wherein the distalizer is made from a metal or a polymer or both.

6. The method according to claim 1, wherein the arm is integrally formed with the mesial element.

7. The method according to claim 1, wherein the distal element and/or the mesial element is molded.

8. A distalizer obtainable by a method according to claim 1.

9. A method of assembling a distalizer, the method comprising:
   providing an arm connecting a distal element with a mesial element, the mesial element having a base for attachment to an upper canine and the distal element having a base for attachment to an upper molar, the arm comprising a ball member at one end of the arm and the distal element comprising a receptacle for receiving the ball member, wherein the ball member is substantially spherical with two diametrically opposed planar surfaces and the receptacle has a shape that is substantially complementary to the shape of the ball member, providing the receptacle with a receptacle opening large enough to introduce the ball member into the receptacle without substantial deformation of the receptacle, introducing the ball member into the receptacle, and reducing the opening of the receptacle by plastically deforming only a portion of a border of the receptacle by coining.

10. The method according to claim 9, wherein the distalizer is made from metal.

11. The method according to claim 9, wherein the plastically deforming the border includes heating the border.

12. The method according to claim 9, wherein the arm is integrally formed with the mesial element.

\* \* \* \* \*